(12) United States Patent
Hanson et al.

(10) Patent No.: US 8,084,511 B2
(45) Date of Patent: Dec. 27, 2011

(54) FLAME RETARDANTS FOR USE IN STYRENIC FOAMS

(75) Inventors: Mark V. Hanson, West Lafayette, IN (US); Stephen B. Falloon, Lafayette, IN (US); Wayne Meyer, West Lafayette, IN (US)

(73) Assignee: Chemtura Corporation, Middlebury, CT (US)

( * ) Notice: Subject to any disclaimer, the term of this patent is extended or adjusted under 35 U.S.C. 154(b) by 708 days.

(21) Appl. No.: 11/998,493

(22) Filed: Nov. 30, 2007

(65) Prior Publication Data

US 2008/0221230 A1 Sep. 11, 2008

(51) Int. Cl.
*C08J 9/00* (2006.01)
*C07C 43/225* (2006.01)

(52) U.S. Cl. ............ 521/83; 521/88; 521/146; 524/464; 524/469; 524/577

(58) Field of Classification Search .................. 521/83, 521/88, 146; 524/464, 469, 577
See application file for complete search history.

(56) References Cited

U.S. PATENT DOCUMENTS

| | | | | |
|---|---|---|---|---|
| 2,488,499 | A | 11/1949 | Moyle | 260/613 |
| 2,979,445 | A * | 4/1961 | Lavigne et al. | 204/157.63 |
| 3,717,609 | A | 2/1973 | Kutner | 524/180 |
| 3,787,506 | A | 1/1974 | Ungefug et al. | 260/613 |
| 3,883,481 | A | 5/1975 | Kopetz et al. | |
| 4,272,583 | A | 6/1981 | Hahn et al. | 428/407 |
| 4,346,052 | A * | 8/1982 | Knox | 264/211 |
| 4,417,003 | A | 11/1983 | Schwarz | |
| 5,030,663 | A | 7/1991 | Sonnenberg et al. | |
| 5,171,757 | A * | 12/1992 | Stobby et al. | 521/85 |
| 6,579,911 | B1 * | 6/2003 | Vo et al. | 521/85 |
| 2003/0195286 | A1 | 10/2003 | De Schryver | |

FOREIGN PATENT DOCUMENTS

| | | |
|---|---|---|
| DE | 19630925 | 2/1998 |
| FR | 2219179 | 5/1976 |
| GB | 1182964 | 3/1970 |
| GB | 1 497 319 | 1/1978 |
| JP | 57038831 | 3/1982 |

OTHER PUBLICATIONS

Taylor et al., A study of flame retardant action of haloaromatic allyl ethers, Fire Proc. Eur. Conf. Flammability Fire Retard., 2$^{nd}$ (1980) pp. 81-88 (1978).

* cited by examiner

*Primary Examiner* — Irina S Zemel
(74) *Attorney, Agent, or Firm* — Joseph Suhadolnik

(57) ABSTRACT

The invention is a flame retardant for styrene foams. The flame retardant contains both aromatic bromine and an olefin. The olefin is an internal olefin. Desirable flame retardants are selected from:
formula I:

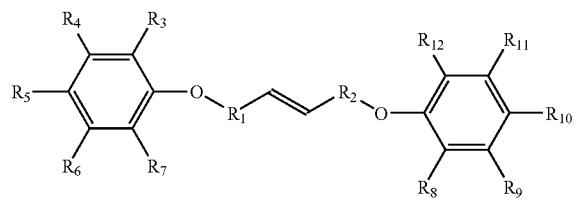

wherein $R_1$ is $C_1$-$C_6$ and optionally containing a heteroatom or olefin; $R_2$ is $C_1$-$C_6$ and optionally containing a heteroatom or olefin; and $R_3$-$R_{12}$ is H, $C_1$-$C_6$ (optionally containing a heteroatom), or halogen; and further wherein the compound of formula I is present in a concentration of at least 50 percent of a trans isomer;
formula II:

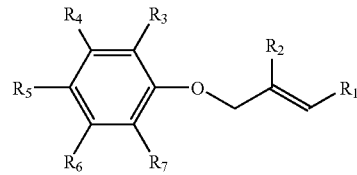

wherein $R_1$ is Halogen, $C_1$-$C_6$ and optionally containing a heteroatom or olefin; $R_2$ is Halogen, $C_1$-$C_6$ and optionally containing a heteroatom or olefin; and $R_3$-$R_7$ is H, $C_1$-$C_6$ (optionally containing a heteroatom), or halogen; and
formula III:

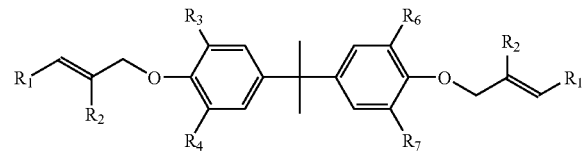

wherein $R_1$ is Halogen, $C_1$-$C_6$ and optionally containing a heteroatom or olefin; $R_2$ is Halogen, H, $C_1$-$C_6$ and optionally containing a heteroatom or olefin; and $R_3$-$R_6$ is H, halogen.

5 Claims, No Drawings

FLAME RETARDANTS FOR USE IN STYRENIC FOAMS

BACKGROUND OF THE INVENTION

1. Field of the Invention

The invention is a flame retardant for styrenic resins containing both aromatic bromine and an olefin. More specifically, the olefin contains an internal olefin instead of a terminal olefin.

2. Description of the Background Art

Styrenic resins or styrenes are well known synthetic organic polymers. Styrenic resins are thermoplastics and have excellent mechanical properties as well as good chemical resistance. The properties that make styrenes useful for many applications as solid polymers also make them very desirable as foamed polymers.

A number of processes have been developed over the last forty years to prepare styrenic foams for a variety of applications. Two particularly useful processes have been developed to make extruded polystyrene foam (XPS) and expanded polystyrene foam (EPS). Extruded polystyrene foam and expanded polystyrene foam are used in industry for a variety of commercial applications. Many of those applications require the foam to be flame retardant to meet specific standards.

The most commonly used materials to flame retard polymer resins are halogenated organic compounds and are well known in the literature to be highly effective flame retardants. Brominated organic compounds are widely used in styrenic resins and foams to provide ignition resistance.

Haloaromatic allyl ethers are known to be acceptable flame retardants for use with expanded polystyrene foam. In known examples, the allyl ether is typically a terminal olefin rather than an internal olefin. Golborn and Taylor studied these systems and proposed a mechanism for the flame retardant action. However, they did not report any examples with an internal olefin or postulate whether the mechanism is applicable to a compound with an internal olefin.

Allylic ethers with a terminal olefin are known to have flame retardant activity in styrenic foams such as expanded polystyrene foam. However, these compounds are not widely used in applications with expanded polystyrene foam. The primary reason that terminal olefin allyl ether compounds are not acceptable is their reactivity and the method by which expanded polystyrene foam is prepared. Expanded polystyrene foam is most commonly prepared by a one step polymerization of styrene monomer. In this method the flame retardant and other additives are added to styrene monomer prior to reaction, and then the styrene is polymerized in water to form beads. The additives, including the flame retardant, are present during the polymerization and are thus incorporated into the beads.

Olefins, other than the styrene monomer, often act as chain transfer agents during polymerization resulting in lower molecular weights of the polystyrene. Lower molecular weight polystyrene typically shows a decrease in the physical properties of the polystyrene. While not wishing to be bound by theory, it is hypothesized that terminal olefins are more readily accessible to participate as chain transfer agents in the polymerization reaction. Internal olefins are more sterically hindered and less accessible to the growing polymer chains and thus are less likely to act as chain transfer agents. Therefore, known allylic ethers with a terminal olefin are generally not considered suitable flame retardants for this application.

The compound 1,4-bis(2,4,6-tribromophenoxy)-2-butene and its flame retardant activity is acknowledged in U.S. Pat. Nos. 2,488,499 and 3,787,506. However, U.S. Pat. No. 3,787,506 states that the compound is not suitable for use in styrenic applications due to its low thermal stability. This compound can be prepared using either cis-1,4-dichloro-2-butene or trans-1,4-dichloro-2-butene. This stereochemistry is maintained during the reaction resulting in cis/trans isomers in the product. No mention is made in these patents to a specific isomer being used in the synthesis, nor is there any indication that the inventors recognized that different isomers have different properties such as thermal stability.

Hexabromocyclododecane (HBCD) in particular was discovered to be a suitable flame retardant for styrenic polymers in general and more specifically for styrenic foams. HBCD is a highly brominated aliphatic compound with an unusually high thermal stability. The high thermal stability and bromine content of HBCD result in excellent performance at low loading levels with a minimum effect on polymer properties. Thus, HBCD has become the material of choice with flame retarding styrenic foams. HBCD has the particularly important properties of high flame retardant efficiency at low concentrations and high thermal stability.

Other flame retardants have been proposed and tested in styrenic foams. Representative examples can be found in the following patent documents of DE1469819, DE2813872, U.S. Pat. No. 4,272,583, DE19630925, GB1182964, FR2138745, JP53008663, and JP57038831. For the most part, the most efficient known flame retardants contain aromatic and/or aliphatic bromine.

The industry is particularly interested in compounds which contain both aromatic bromine and allylic ether. Two examples of this combination are tetrabromobisphenol A allyl ether and tribromophenol allyl ether. However, known examples of these two compounds are unsatisfactory as alternatives to HBCD. These two compounds exhibit unsatisfactory thermal stability, efficiency, and cost. These two compounds also exhibit decreased mechanical properties and deterioration of molecular weight while also presenting concerns regarding their impact on health and the environment.

Recently there have been concerns about the health and environmental impact of some flame retardants including HBCD. Although scientific studies have not necessarily shown significant risks to human health or the environment, there are ongoing reviews by various regulatory agencies that may result in reduced usage of HBCD. In the event that these agencies limit the usage of HBCD, extruded polystyrene foam and expanded polystyrene foam manufacturers may be required to choose an alternative flame retardant, and many may adopt a substitute before any regulatory mandate. Thus, there exists a need for a flame retardant alternative to HBCD that is more environmentally friendly and maintains all of the performance properties of HBCD.

SUMMARY OF THE INVENTION

The invention is a flame retardant containing both aromatic bromine and an olefin. The olefin is an internal olefin.

The flame retardant compound is desirably a member selected from the group consisting of at least one of the following compounds.

The first compound is represented by formula I, wherein the compound of formula I is present in a concentration of at least 50 percent of a trans isomer:

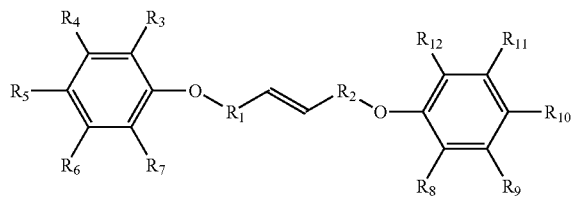

$R_1$ is $C_1$-$C_6$ and optionally containing a heteroatom or olefin.
$R_2$ is $C_1$-$C_6$ and optionally containing a heteroatom or olefin.
$R_3$-$R_{12}$ is H, $C_1$-$C_6$ (optionally containing a heteroatom), or halogen The second compound is represented by formula II.

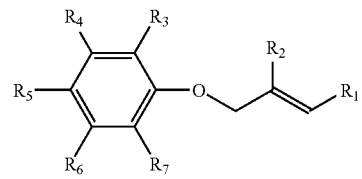

$R_1$ is Halogen, $C_1$-$C_6$ and optionally containing a heteroatom or olefin.
$R_2$ is Halogen, $C_1$-$C_6$ and optionally containing a heteroatom or olefin.
$R_3$-$R_7$ is H, $C_1$-$C_6$ (optionally containing a heteroatom), or halogen.

The third compound is represented by formula III.

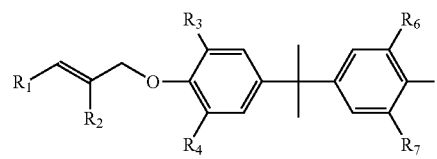

$R_1$ is Halogen, $C_1$-$C_6$ and optionally containing a heteroatom or olefin.
$R_2$ is Halogen, H, $C_1$-$C_6$ and optionally containing a heteroatom or olefin.
$R_3$-$R_6$ is H, halogen.

DETAILED DESCRIPTION OF THE INVENTION

The invention is a flame retardant containing both aromatic bromine and an olefin. The olefin is an internal olefin instead of a terminal olefin. The internal olefin provides the invention with desirable thermal stability, efficiency, and cost. The invention also exhibits desirable mechanical properties with minimal molecular weight deterioration and minimal impact on health and the environment.

The flame retardant compound is desirably a member selected from the group consisting of at least one of the following compounds. The first compound is represented by formula I, wherein the compound of formula I is present in a concentration of at least 50 percent of a trans isomer:

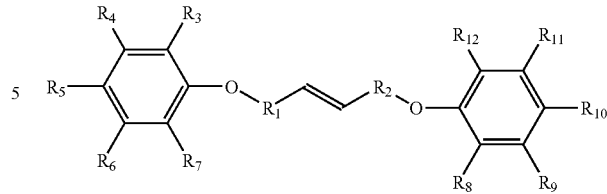

$R_1$ is $C_1$-$C_6$ and optionally containing a heteroatom or olefin.
$R_2$ is $C_1$-$C_6$ and optionally containing a heteroatom or olefin.
$R_3$-$R_{12}$ is H, $C_1$-$C_6$ (optionally containing a heteroatom), or halogen.

The second compound is represented by formula II.

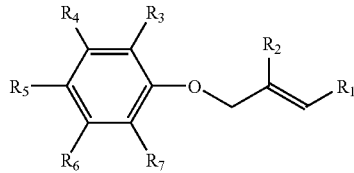

$R_1$ is Halogen, $C_1$-$C_6$ and optionally containing a heteroatom or olefin.
$R_2$=Halogen, $C_1$-$C_6$ and optionally containing a heteroatom or olefin.
$R_3$-$R_7$ is H, $C_1$-$C_6$ (optionally containing a heteroatom), or halogen.

The third compound is represented by formula III.

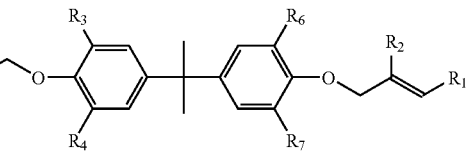

$R_1$ is Halogen, $C_1$-$C_6$ and optionally containing a heteroatom or olefin.
$R_2$ is Halogen, H, $C_1$-$C_6$ and optionally containing a heteroatom or olefin.
$R_3$-$R_6$ is H, halogen.

The compounds of the invention are compounds in which an olefin forms an allylic ether with a brominated aromatic ring or rings. In known examples of haloaromatic allyl ethers used as flame retardants, the allyl ether has a terminal olefin rather than an internal olefin. The expectation of compounds having an internal olefin is that efficiency is diminished due to steric hindrance caused by the internal olefins. This expectation is particularly relevant with the preferred compounds of this invention. Therefore, it is surprising that the compounds of the invention are at least as efficient as molecules that contain terminal allylic ethers.

Particularly desirable flame retardant compounds having internal olefins are presented in Table 1. The olefin-containing compounds of Table 1 are a selection of the desirable compounds of this invention. The non-olefin-containing compounds are provided for comparison.

TABLE 1

| Compound | LOI @ 5 phr | TGA 5% Loss |
|---|---|---|
| 2,4,6-tribromophenyl ether of 2-butene-1,4-diyl (bis(2,4,6-tribromophenoxy)-2-butene) | 30.2 | 221° C. |
| 2,4,6-tribromophenyl cinnamyl ether | 34.5 | 182° C. |
| 2,4,6-tribromophenyl 3-chloroallyl ether | 32.5 | 157° C. |
| bis[3,5-dibromo-4-(2-bromoallyloxy)phenyl]propane | 32.0 | 229° C. |
| 1,4-bis(2,4,6-tribromophenoxy)butane | 21.0 | 214° C. |
| 1,2-bis(pentabromophenyl)ethane | 22.0 | 347° C. |

The limiting oxygen index (LOI) test is a useful indication of flame retardant efficiency for screening purposes. This test measures the percentage of oxygen in the atmosphere required to support burning of a material such as a flame retarded styrenic foam. The higher the LOI, the richer in oxygen the atmosphere must be for combustion to occur. Thus, in comparing flame retarded materials, articles which have a higher LOI can be said to have more efficient flame retardant activity for a given concentration or "load level." Table 1 illustrates that the presence of an allylic ether olefin in compounds results in a higher LOI than occurs with comparable structures not having an olefin. In particular, Table 1 shows that internal olefins provide high LOI values.

Thermal stability is another important characteristic for comparison of flame retardant compounds. Typically, thermal stability is measured using thermogravimetric analysis (TGA) in a dynamic mode. Values from this test are reported as the temperature at which the test specimen lost 5 percent of its initial weight.

For purposes of screening potential flame retardants for styrenic foams, it is desirable to have an LOI of greater than 26 at 5phr and a 5 percent weight loss based on a TGA of greater than 215° C. in order to be considered comparable to HBCD in end use with expanded polystyrene foam. For extruded polystyrene foam, a 5 percent weight loss in a TGA of greater than 240° C. is desirable in order to be considered comparable to HBCD.

The compounds of Table 1 with LOI greater than 26 were found acceptable for applications with expanded polystyrene foam. Of these, a particularly preferred compound is 1,4-bis (2,4,6-tribromophenoxy)-2-butene. This compound and its flame retardant activity are acknowledged in U.S. Pat. Nos.

2,488,499 and 3,787,506. However, U.S. Pat. No. 3,787,506 states that the compound is not suitable for use in styrenic applications due to its low thermal stability.

The compound 1,4-bis(2,4,6-tribromophenoxy)-2-butene can be prepared using either cis-1,4-dichloro-2-butene or trans-1,4-dichloro-2-butene. This stereochemistry is maintained during the reaction resulting in cis/trans isomers in the product. We discovered that the isomers do have different thermal stabilities and that the trans isomer is preferred for its better thermal stability. We discovered that a desirable level of activity of this compound to retard flame in polystyrene foam occurs when at least 50 percent of the compound is present in the trans isomer. The activity is desirably enhanced when the compound is present in its preferred concentration of the trans isomer of at least 80 percent.

The compounds of this invention are particularly desirable for applications with expanded polystyrene foam. However, these compounds are also useful in applications with extruded polystyrene foam. Applications with extruded polystyrene foam require slightly higher thermal stability than do applications with expanded polystyrene foam.

The thermal stability for compounds used in applications with extruded polystyrene foam is desirably a 5 percent weight loss as determined by a TGA of greater than 240° C. Flammability screening requirements are the same as for expanded polystyrene foam in that it is desirable to have a LOI greater than 26. We found that a new compound derived from the preferred 1,4-bis(2,4,6-tribromophenoxy)-2-butene meets both the thermal stability and LOI requirements for applications with extruded polystyrene foam. The compound is as follows.

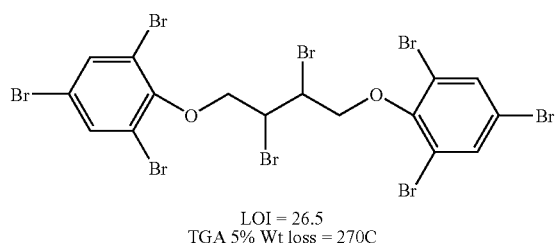

LOI = 26.5
TGA 5% Wt loss = 270C

The addition of bromine across the internal olefin of this compound and the compounds described above increases the thermal stability relative to the starting material. Therefore, such derivative compounds, as represented by formula IV, perform well with extruded polystyrene foam and expanded polystyrene foam.

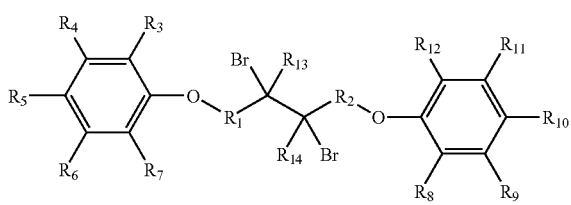

$R_1$ is $C_1$-$C_6$ and optionally containing a heteroatom or olefin.
$R_2$ is $C_1$-$C_6$ and optionally containing a heteroatom or olefin
$R_3$-$R_{12}$ is H, $C_1$-$C_6$ (optionally containing a heteroatom) or halogen.
$R_{13}$-$R_{14}$ is H or Br.

EXAMPLE 1

1,4-bis(2,4,6-tribromophenoxy)-2-butene

Example 1 illustrates the synthesis of the preferred compound of the invention. This compound is 1,4-bis(2,4,6-tribromophenoxy)-2-butene. This example also illustrates the thermal stability of the compound.

A 5 L four-neck flask was charged with tribromophenol (590.0 g, 1.783 mol), isopropanol (1500 g), water (1300 g); and 50% NaOH (150.0 g, 1.875 mol). The flask was fitted with mechanical stirring, a condenser, heating mantle, and temperature probe. The mixture was heated to 70° C. over ca. one hour. Compound 1,4-dichloro-2-butene (mixture of trans and cis, 111.5 g, 0.892 mol) was added and a precipitate formed within two minutes. The material eventually formed a thick slurry and was stirred for two hours. The slurry was filtered hot over a fritted funnel, washed with water (2×1 L), and dried in a 90° C. oven for 14 to 16 hours to give a white powder (587.3 g, 0.8229 mol, 92%).

In order to test thermal stability properties of the two isomers, TGA experiments were used. In this case, isothermal TGA was employed where a sample was held at constant temperature for a specified time. The weight remaining at the end of the hold time gives an indication of the relative thermal stabilities of the isomers. The more weight remaining, the more thermally stable the material. Table 2 shows the results of experiments on samples of 1,4-bis(2,4,6-tribromophenoxy)-2-butene containing either cis or trans or a mix of cis and trans isomers. These materials were made from cis or trans 1,4-dichloro-2-butene.

TABLE 2

| % Trans Isomer | Isothermal TGA 200 C. for 30 min |
| --- | --- |
| 0 | 26 |
| 25 | 29.6 |
| 50 | 31.1 |
| 75 | 30.9 |
| 92.3 | 75.6 |
| 94.7 | 80.6 |
| 97 | 79.8 |

The data of Table 2 clearly show that the trans isomer is intrinsically more thermally stable than the cis isomer. Further, samples containing greater than approximately 90% trans isomer result in material that is quite thermally stable and acceptable for applications with expanded polystyrene foam.

EXAMPLE 2

1,4-bis(2,4,6-tribromophenoxy)-2,3-dibromobutane

Example 2 illustrates the synthesis of a desirable compound of the invention. This compound is 1,4-bis(2,4,6-tribromophenoxy)-2,3-dibromobutane.

A 500 mL four-neck flask was charged with 1,4-bis(2,4,6-tribromophenoxy)-2-butene, (37.8 g, 0.0529 mol) and 1,2-dichloroethane (160 g). The flask was fitted with mechanical stirring, a condenser, heating mantle, temperature probe, and dropping funnel with bromine (10.7 g, 0.0669 mol). The mixture was heated to 50° C. over ca. 30 minutes. Bromine was then added drop-wise over ca. 30 minutes and stirred for 2.5 hours. An additional charge of bromine was added (0.7 g, 0.004 mol) and stirred another hour. The reaction was then cooled to ambient temperature and MeOH (50 mL) was added. The slurry was filtered over frit and washed with MeOH (100 mL). The material was then dried at 90° C. 14-16 hours to give an off-white powder (33.9 g, 0.0388 mol, 73%). The resulting compound had a OBr=70.5%, a TGA of 5% wt loss at 276° C., and an isothermal TGA (30min @220° C.) of 95.6% wt retention.

EXAMPLE 3

1,4-bis(2,4,6-tribromophenoxy)-2,3-dibromobutane

Example 2 illustrates the synthesis of a desirable compound of the invention. This compound is 1,4-bis(2,4,6-tribromophenoxy)-2,3-dibromobutane.

A 500 mL four-neck flask was charged with 1,4-bis(2,4,6-tribromophenoxy)-2-butene, (40.0 g, 0.0560 mol), bromine (12.5 g, 0.078 mol), and dichloromethane (160 g). The reaction was heated at 40° C. for four hours. The mixture was cooled to ambient temperature and excess bromine was neutralized with hydrazine (35% in water, ca. 1-2 mL). The solution was pressure filter through a cloth filter (20 psi) and washed with water (50 g). The solid was dried at 95-100° C. overnight to give a white powder (38.5 g, 78%). The resulting compound had a OBr of 71.7%, a 5% TGA loss at 279° C., an isothermal TGA (30 min @220° C.) at 95.6% wt retention, and an LOI (2.0% Br in PS) 25.5.

EXAMPLE 4

Preparation of Hand-Cast Foam

Typical laboratory hand-cast foams were prepared for LOI determination using the formulations listed below. Lab preparation yielded foams with comparable densities. The foams were then evaluated by ASTM D2863-00 and UL-94. ASTM D2863-00 is a test method used to determine the Limiting Oxygen Index (LOI).

Polystyrene was extruded with 1,4-bis(2,4,6-tribromophenoxy)-2,3-dibromobutane to generate beads from which LOI bars were compression molded. The following conditions were employed on an 18 mm single screw extruder:

Extruder Temperatures
Zone 1=160° C.
Zone 2=220° C.
Zone 3=220° C.
Die=220° C.
Extruder speed=60 rpm
Extruder amps=40-60
Melt Pressure=940-1160 psi The pellets were compression molded into bars. The bars were then evaluated by ASTM D2863-00 and UL-94. The results are presented in Table 3.

TABLE 3

| Flame Retardant | HBCD | 1,4-bis(2,4,6-tribromophenoxy)-2,3-dibromobutane |
|---|---|---|
| Load Level, Wt % | | |
| FR | 2.68 | 2.84 |
| MgO | 0.1 | 0.1 |
| CaSt | 0.1 | 0.1 |
| DI-Cup | / | / |
| CCDFB-90 | / | / |
| PS 1600 | 97.12 | 96.96 |

TABLE 3-continued

| Flame Retardant | HBCD | | | 1,4-bis(2,4,6-tribromophenoxy)-2,3-dibromobutane | | |
|---|---|---|---|---|---|---|
| MFI, g/10 min | 8.3 | 9.7 | 10.5 | 7.2 | 10.4 | 12.8 |
| LOI | 28.4 | | 28.4 | 24.6 | | 26.5 |

TABLE 4

| Formulations | |
|---|---|
| | Hand Cast |
| Nova 1994 PS resin | 40 g |
| Methylene chloride | 178 g |
| Flame Retardant | 0.2 g-10 g |
| Pentane | 4 g |

EXAMPLE 5

Comparison with HBCD

Example 5 conducted solution polymerization experiments comparing HBCD, 1,4-bis(2,4,6-tribromophenoxy)-2-butene and tetrabromobisphenol A bis allyl ether. The tetrabromobisphenol A bis allyl ether contains terminal olefins.

As described previously, allylic ethers which have terminal olefin have been known in the art to have flame retardant activity in styrenic foams such as expanded polystyrene foam. However, these compounds are not widely used in applications with expanded polystyrene foam. Terminal olefins are understood to be more readily accessible to participate as chain transfer agents in the polymerization reaction. Internal olefins are understood to be more sterically hindered and less accessible to the growing polymer chains and thus are less likely to act as chain transfer agents.

The results are shown in Table 5.

TABLE 5

| | Run 1 | Run 2 | Run 3 | Run 4 | Run 5 | Run 6 |
|---|---|---|---|---|---|---|
| Temp, ° C. | 90 | 90 | 90 | 90 | 90 | 90 |
| Styrene, g | 8.67 | 8.6 | 8.6 | 8.6 | 8.89 | 8.6 |
| PhCl, g | 6.8 | 6.76 | 6.72 | 6.7 | 6.68 | 6.78 |
| VAZO-52, g | 0.005 | 0.005 | 0.004 | 0.005 | 0.006 | 0.006 |
| HBCD, g | | 0.22 | | | | |
| Terminal olefin, g | | | | 0.3 | | |
| Internal olefin, g | | | | | | 0.3 |
| Yield, g | 2.18 | 2.51 | 1.97 | 2.57 | 2.29 | 2.57 |
| Yield % | 25.1 | 29.2 | 22.9 | 29.9 | 25.7 | 29.9 |
| GPC Mw | 148,000 | 149,300 | 142,000 | 112,700 | 146,900 | 141,100 |

The data of Table 5 indicate that the molecular weight of the polystyrene is decreased when tetrabromobisphenol A bis allyl ether is used as the flame retardant.

We claim as follows:

1. A flame-retarded foam comprising:
an extruded or expanded styrene polymer foam;
and cis and trans isomers a flame retardant compound of formula I:

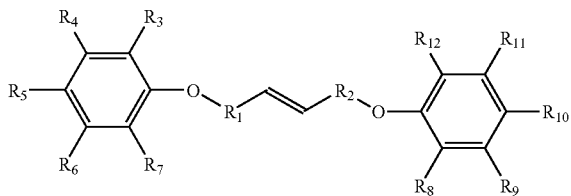

wherein:
$R_1$ is $C_1$-$C_6$ and optionally containing a heteroatom or olefin;
$R_2$ is $C_1$-$C_6$ and optionally containing a heteroatom or olefin; and
$R_3$-$R_{12}$ is H, $C_1$-$C_6$ optionally containing a heteroatom, or halogen;
and further wherein 90 to 97 percent of the cis and trans isomers of said compound of formula I are trans isomer.

2. The flame-retarded foam of claim 1 wherein said polystyrene foam is expanded polystyrene foam.

3. The flame-retarded foam of claim 1 comprising an extruded or expanded styrene polymer foam and cis and trans isomers of 1,4-bis(2,4,6-tribromophenoxy)-2-butene as flame retardant wherein 90 to 97 percent of the cis and trans isomers of 1,4-bis(2,4,6-tribromophenoxy)-2-butene are trans isomer.

4. The flame-retarded foam of claim 1 wherein 92 to 97 percent of the cis and trans isomers of said compound of formula I are trans isomer.

5. The flame-retarded foam of claim 3 wherein 92 to 97 percent of the cis and trans isomers of 1,4-bis(2,4,6-tribromophenoxy)-2-butene are trans isomer.

* * * * *